United States Patent
Campbell et al.

(10) Patent No.: US 8,748,355 B2
(45) Date of Patent: Jun. 10, 2014

(54) ANTIGEN DETECTION

(75) Inventors: Colin Campbell, Midlothian (GB); Peter Ghazal, Edinburgh (GB); Juraj Petrik, Peebles (GB); Janine Scott Robb, Edinburgh (GB)

(73) Assignee: University Court of the University of Edinburgh (GB)

( * ) Notice: Subject to any disclaimer, the term of this patent is extended or adjusted under 35 U.S.C. 154(b) by 1471 days.

(21) Appl. No.: 11/886,245

(22) PCT Filed: Mar. 23, 2006

(86) PCT No.: PCT/GB2006/001044
§ 371 (c)(1),
(2), (4) Date: Apr. 17, 2008

(87) PCT Pub. No.: WO2006/100477
PCT Pub. Date: Sep. 28, 2006

(65) Prior Publication Data
US 2008/0318798 A1    Dec. 25, 2008

(30) Foreign Application Priority Data
Mar. 24, 2005 (GB) .................. 0506183.3

(51) Int. Cl.
*C40B 30/06* (2006.01)
(52) U.S. Cl.
USPC .......................................................... 506/10
(58) Field of Classification Search
None
See application file for complete search history.

(56) References Cited

U.S. PATENT DOCUMENTS

| | | | |
|---|---|---|---|
| 4,770,856 A | 9/1988 | Uthemann et al. | |
| 4,851,210 A | 7/1989 | Hewett | |
| 5,338,689 A | 8/1994 | Yves et al. | |
| 5,552,064 A | 9/1996 | Chachowski et al. | |
| 2001/0046453 A1 | 11/2001 | Weigl et al. | |
| 2003/0224457 A1* | 12/2003 | Hurt et al. | 435/7.2 |
| 2004/0132214 A1 | 7/2004 | Lin et al. | |
| 2005/0014171 A1* | 1/2005 | Fraser et al. | 435/6 |

FOREIGN PATENT DOCUMENTS

| | | |
|---|---|---|
| EP | 0223978 A1 | 6/1987 |
| EP | 0223978 B1 | 8/1992 |
| WO | WO 02/42775 A2 | 5/2002 |
| WO | WO 02/059583 A1 | 8/2002 |
| WO | WO 03/023377 A1 | 3/2003 |

OTHER PUBLICATIONS

Emmelkarmp (Nov. 26, 2004) Electrophoresis vol. 25 pp. 3740 to 3745.*
Baecher-Allan (Aug. 1, 2001) The Journal of Immunology vol. 167 pp. 1245 to 1253.*
Jayakumar et al. (2003) Biochimica et Biophysica Acta vol. 1622 pp. 20 to 28.*

(Continued)

*Primary Examiner* — Christian Boesen
(74) *Attorney, Agent, or Firm* — Myers Bigel Sibley & Sajovec, P.A.

(57) ABSTRACT

The present invention relates to methods of detecting specific cell surface antigens present in a sample of cells being tested and in particular blood group antigens, which methods do not employ the addition of extrinsic labels to detect said cell surface antigens. Typically detection is carried out using an intrinsic fluorescence capability of the cells being tested.

18 Claims, 14 Drawing Sheets

(56) References Cited

OTHER PUBLICATIONS

Du et al. "Hybridization-Based Unquenching of DNA Hairpins on Au Surfaces: Prototypical "Molecular Beacon" Biosensors", *J. Am. Chem. Soc.* 125:4012-4013 (2003).

Neuschafer et al. "Evanescent resonator chips" a universal platform with superior sensitivity for fluorescence-based microarrays, *Biosensors and Bioelectronics* 18:489-497 (2003).

Emmelkamp et al. "The potential of autofluorescence for the detection of single living cells for label-free cell sorting in microfluidic systems", *Eletrophoresis* 25:3740-3745 (2004).

Morhard et al. "Immobilization of antibodies in micropatterns for cell detection by optical diffraction", *Sensors and Actuators B* 70:232-242 (2000).

DaCosta et al. "Correlation of Autofluorescence (AF) and ultrastructures of ex vivo colorectal tissues and isolated living epithelial cells from primary cell cultures (PCC) of normal colon and hyperplastic and dysplastic polyp: Implications for early diagnosis, altered cell metabolism, and cytopathology", *Gastroenterology* 116:A393 (1999).

Campbell et al. "Cell Interaction Microarray for Blood Phenotyping", *Anal. Chem.* 78:1930-1938 (2006).

Liu et al. "Direct Visualization of Trapped Erythrocytes in Rat Brain After Focal Ischemia and Reperfusion", *J. of Cerebral Blood Flow and Metabolism* 22:1222-1230 (2002).

International Search Report corresponding to International Application No. PCT/GB2006/001044 mailed May 24, 2006.

Written Opinion of the International Searching Authority corresponding to International Application No. PCT/GB2006/001044 mailed May 24, 2006.

Belov et al. "Immunophenotyping of Leukemias Using a Cluster of Differentiation", *Cancer Research* 61:4483-4489 (2001).

Duburcq et al. "Peptide-Protein Microarrays for the Simultaneous Detection of Pathogen Infections", *Bioconjugate Chem.* 15:307-316 (2004).

Haab et al. "Protein microarrays for highly parallel detection and quantitation of specific proteins and antibodies in complex solutions", *Genome Biology* 2(2):research 0004.1-0004.13 (2001).

Melnyk et al. "Peptide Arrays for Highly Sensitive and Specific Antibody-Binding Fluorescence Assays", *Bioconiugate Chem.* 13:713-720 (2002).

Mezzasoma et al. "Antigen Microarrays for Serodiagnosis of Infectious Diseases", *Clinical Chemistry* 48(1):121-130 (2002).

J. Petrik "Microarray technology: the future of blood testing?", *Vox Sanquinis* 80:1-11 (2001).

Robinson et al. "Autoantigen microarrays for multiplex characterization of autoantibody responses", *Nature Medicine* 8(3):1-7 (2002).

\* cited by examiner

ANTIGEN DETECTION

CROSS-REFERENCE TO RELATED APPLICATIONS

This application is a 35 U.S.C. §371 national phase application of PCT Application No. PCT/GB2006/001044, filed on Mar. 23, 2006, which claims priority from Great Britain Application Serial No. 0506183.3 filed on Mar. 24, 2005, the disclosures and contents of which are incorporated by reference herein in their entireties. The above-referenced PCT International Application was published in the English language as International Publication No. WO 2006/100477A1.

FIELD OF THE INVENTION

The present invention relates to methods of detecting specific cell surface antigens present in a sample of cells being tested and in particular blood group antigens, which methods do not employ the addition of extrinsic labels to detect said cell surface antigens. Typically detection is carried out using an intrinsic fluorescence capability of the cells being tested.

BACKGROUND TO THE INVENTION

Blood typing in the clinical and transfusion fields is typically currently carried out using agglutination assays either in multi well plates, see for example, U.S. Pat. No. 4,770,856, or in card/column format (e.g. U.S. Pat. No. 5,552,064 and U.S. Pat. No. 5,338,689). Additionally, multiplexed typing can be carried out using flow cytometry, but this requires fluorescent labelling and relatively complex apparatus.

U.S. Pat. No. 4,851,210 describes a blood-typing device based on capillary flow through a membrane, which comprises an array of type-specific antibodies capable of immuno-specifically binding red blood cells. Bound red blood cells may be detected visually by the red colour of the cells, or by using detectable agents such as dyes, detectably labelled antibodies, or detectably labelled affinity ligands.

EP0223978 discloses methods and devices for determining blood group classifications from blood or serum samples, utilising a porous substrate comprising one or more antibodies bound thereto in delimited adsorption areas. Bound red blood cells are detected by a colour signal from erythrocytes bound to the antibodies.

Nevertheless, any current systems which rely on detection by eye generally require a relatively large sample of blood and/or a sufficiently large area for binding the red blood cells, in order that the colour may easily be discernable by eye which it will be appreciated can be undesirable. Moreover, visual detection may not be preferable as this can result in human error and an incorrect interpretation of results. Thus, it may be desirable to utilise an automated system.

It is an object of the present invention to obviate and/or mitigate at least one of the aforementioned disadvantages.

SUMMARY OF THE INVENTION

The present invention is based in part on observations by the present inventors that certain cells are capable of autofluorescing. That is, cells can be exposed to light of a first wavelength and can fluoresce at a second wavelength, which can be detected, using, for example, an appropriate photo elector apparatus. In this manner cells may be detected without the use of additional labelling agents.

In a first aspect there is provided a method for determining a blood group of a sample of blood, comprising the steps of:
 a) providing a sample of blood comprising red blood cells to a device which comprises a substrate comprising one or more binding agents bound thereto, wherein said binding agents are capable of specifically binding to specific red blood cell group antigens which may be present in the sample of blood;
 b) allowing any red blood cell antigens present in the sample of blood to specifically react with said bound binding agents;
 c) substantially removing or reducing any unbound material from at least an area of the substrate to which said binding agents are bound; and
 d) directly detecting any antigens bound to said binding agents in order to determine a subjects blood group.

The assays of the present invention may be used to detect, for example, any specified blood group antigen. The most common blood group systems are the ABO and D (Rhesus) systems well known in the art, although other systems such as Kell, Duffy, Lewis, Kidd and Fisher are also known and may be tested for or in accordance with the methods described herein. See also Handbook of Transfusion Medicine, McClelland, DBL, Ed; TSO London, 2001.

Typically the binding agents are antibodies or antibody fragments specific for the antigens to be detected. However, other specifically reactive binding agents, such as small molecule antibody mimetics, or receptors from other cells which are capable of binding said antigens may be employed. Lectins may also be employed. However, for simplicity reference hereinafter will be made to antibodies, but this should not be construed as limiting.

In order to detect whether or not a particular antigenic determinant is present in a sample of cells, an antibody or antibody fragment capable of specifically binding to the particular antigen would be provided, bound to the substrate. For example, for detecting cells of the ABO type, the substrate will comprise anti-A and anti-B antibodies. Cells which bind only to the anti-A antibodies will be type A; cells which bind only to the anti-B antibodies will be type B; cells which bind to the anti-A and anti-B antibodies will be type AB; and cells which do not bind to either the anti-A or anti-B antibodies will be type O. With regards to detecting whether or not a sample of blood cells are Rhesus-positive or Rhesus negative, Anti-D, Anti-C and/or Anti-E antibodies will generally be bound to the substrate as the D antigen is the most potent of Rhesus antigens and most commonly involved in sensitisation by transfusion or pregnancy.

As a positive control, in order to ensure that red blood cell antigens are in fact binding, lectins or anti-H may be used. This may be advantageous when neither anti-A or anti-B antibodies bind to the red blood cells, as will be the case when the blood is type O.

The antibodies bound to the substrate may be polyclonal or monoclonal.

Polyclonal antibodies are heterogeneous populations of antibody molecules derived from the sera of animals immunized with an antigen, or an antigenic functional derivative thereof. For the production of polyclonal antibodies, host animals for example rabbits, sheep, pigs, etc., can be immunized by injection with a specific antigen optionally supplemented with adjuvants.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. U.S.A. 80:2026-2030), and the EBV-hybridoma technique (Cole et al., 1985, Monoclonal Anti-bodies and Cancer Therapy, Alan R. Liss, Inc., pp. 77-96).

Such antibodies can be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

In addition, techniques for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454; U.S. Pat. No. 4,816,567) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778: Bird, 1988, Science 242:423-426; Huston et al., 1988, Proc. Natl. Acad. Sci. U.S.A. 85:5879-5883; and Ward et al., 1989, Nature 334:544-546) and for making humanized monoclonal antibodies (U.S. Pat. No. 5,225,539) can be utilized.

Antibody fragments which recognize specific epitopes can be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries can be constructed (Huse et al., 1989, Science, 246:1275-1281) to allow rapid and easy identification of monoclonal Fab fragments with the desired specificity.

Typically, the antibodies are bound to the substrate in an array. As used herein the term "array" refers to a generally ordered arrangement of bound antibodies, that specifically bind to red blood cell antigens, especially cell surface antigens, on a substrate such as glass. Typically the array may be in the form of a series of regularly spaced apart delimited areas to which the antibodies are bound. Such substrate bound antibody arrays may be commonly described as an "antibody chip".

The antibodies may be arranged on for example, a flat or spherical substrate referred hereto as a "chip" so that there are preferably at least one or more different antibodies, more preferably at least about 2 antibodies, still more preferably at least about 4 antibodies are bound to the surface of the substrate. Moreover, each specific antibody may be provided in a number of dilutions and/or repeated a number of times (e.g. 3-10 times), in order to minimise any false positive or negative reactions which may occur, when carrying out a method of detection.

The array can be made of any conventional substrate, for example glass, silicon, silicon oxide, metals and metal oxides either bare or functionalised with functional polymers such as glycidoxypropyltriethoxysilane, poly-1-lysine, aminopropylsilane, carboyxsilane, hydrogels and polymer-brushes, self-assembled monolayers of e.g. functionalised alkyl thiols. In certain embodiments, it may be desirable to utilise gold coated substrates. Fluorescence of cells, especially red blood cells can increase on gold coated substrates in comparison to non-gold coated substrates. Without wishing to be bound by theory, this can be explained in terms of the special optical properties that films of gold exhibit. Within 7 nm of the gold surface, non-radiative energy transfer will occur between the excited fluorophore and the surface and this property has been used to good effect in the design of "molecular beacons" (Du et al., J. Am. Chem. Soc., 2003, 125, 4012-4013). This will result in a quenching of the emitted light and a concomitant decrease in the fluorescent signal associated with a spot. Since red blood-cells are roughly 6-8 μm in diameter and 1 μm in depth, 99% of the cell volume is outside this area, meaning that the signal is not quenched. However, when fluorescence of red cells spotted on gold slides is compared with those on epoxy silane slides, the fluorescence of the blood cells on the gold slides is higher. This can be explained in terms of another optical quality of noble metal films, the ability to form an evanescent field at the surface. The evanescent wave is a non-propogating light wave that extends from the surface for hundreds of nanometers. Positioning of a fluorophore in this field will enhance the intensity of light emitted from it. While the power of the evanescent wave will be dependant on the angle at which the laser strikes the gold surface, there is still likely to be some enhancement even when using a non-optimized scanner as has been shown using slides printed with a grating pattern (Neuschafer, D., Budach, W., Wanke, C., Chibout, S.-D., *Biosens. Bioelectronics* 2003, 18, 489-497). The enhanced fluorescence caused by the excitation of red blood-cells by a surface-confined light wave is what causes the signal from spots of blood on gold to emit a higher intensity of light than on the epoxy-silane coated films. This is a significant advantage of the use of gold as a microarray surface. Again without being bound by theory, the inventors consider that since the difference between fluorescence quenching and evanescent enhancement of signal is caused by a distance dependence, gold is a preferred surface to work with for a range of assays. Gold can be easily functionalised using well established techniques for self assembled monolayer formation (Datwani, S. S., Vijayendran, R. A., Johnson, E., Biondi, S. A., *Langmuir* 2004, 20, 4970-4976), meaning that the distance between a fluorophore and the gold surface can be tuned by, for example, the length of an alkyl chain (Imahori, H. Norieda, H., Nishimura, Y., Yamazaki, I., Higuchi, J., Kato, N., Motohiro, T., Yamada, H., Tamaki, K., Arimura, M., Sakata, Y., *J Phys, Chem. B.* 2000, 104, 1253-1260) and the surface chemistry can be easily controlled by the choice of end group. This approach means that the antibodies used in an assay can be positioned such that red blood cells bind within the evanescent field without being quenched. To take full advantage of this process the surface roughness of the gold may need to be optimised since this will improve the enhancement and the configuration of the microarray scanner would have to be matched to the plasmon resonance angle.

The array can be in any shape that can be read, including planar and spheroid. Preferred substrates are any suitable rigid or semi-rigid support including membranes, filter, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the antibodies are bound. Preferred substrate surface architecture for improving fluorescent detection are described in WO02/059583 and WO03/023377. In certain embodiments, the substrates are preferably optically transparent.

Generally speaking the "antibody chips" of the present invention may comprise small planar substrates, such as 50-100 mm, e.g. 76 mm×15-50 mm, e.g. 26 mm, with spot size between 50 and 1000 µm, and up to 10000 spots of antibodies per slide. Conveniently each antibody may be spotted, printed or otherwise bound to the substrate using known techniques, see for example Michael J. Heller, *Annual Review of Biomedical Engineering*, 2002 Vol. 4: 129-153. DNA Microarray Technology: Devices, Systems and Applications. Angenendt, P.; Glökler, J.; Murpy, D.; Lehrach, H.; Cahill, D. J. *Anal. Biochem.*, 2002, 309, 252-260 Angendt, P.; Glökler, J.; Sobek, J.; Lehrach, H.; Cahill, D. *J. Chromatogr. A*, 2003 100, 997-104. Typical spots are less than 1 mm in diameter, such as less that 500 µm or 100 µm in diameter. In this manner 10 s to 1000 s of antibody spots may be provided in a single array, if so required.

The "antibody chips" of the present invention may also be used to test more than one sample. In this manner, each chip may comprise a plurality of separate arrays on the surface of the substrate, arranged in a manner to allow separate samples to be contacted with each array an in such a way such that the samples do not mix. For example, each array may be bounded by a wall, ridge, dam, hydrophobic zone or the like designed to prevent different samples from coming into contact with one another.

Any antigens present in the sample of blood are allowed to specifically react with said bound antibodies over a period of time, such as 10 seconds to several hours, for example 1 minute to 60 minutes. Typically, this may be carried out at room temperature, but may also be carried out at, for example, 37° C.

Removal of unbound material may be achieved by, for example, washing the surface of the substrate with a solution such as water or saline, by blowing or sucking air across the surface of the substrate, or by using centrifugation, or shaking to dispel unbound material from the surface of the substrate. Moreover, areas of the substrate outwith the delimited areas to which the antibodies are bound, may be porous to cells from the sample being tested, such that cells which do not come into contact with the antibodies pass through the substrate and are thereby easily removed.

Direct detection is carried out by irradiating the surface of the substrate and detecting any fluorescence in areas of the substrate upon which antibody has been bound. Surprisingly, the inventors have observed that red blood cells and other eukaryotic cells, such as macrophages fluoresce when irradiated with light of a shorter wavelength to that used for detection. For example red blood cells may be irradiated or excited with light of wavelength about 420 nm, 488 nm, 543 nm or 580 nm and emission detected at a longer wavelength such as 530 nm if excited at 488 nm or 570-585 nm if excited at 543 nm.

Thus, if any red blood cells bind to an antibody bound to the surface of the substrate, this may be detected by a fluorescent signal. By knowing the position of each specific antibody on the substrate, it is possible to identify which antigens are present on the surface of the red blood cells being tested and thus identify the blood group of the sample of blood being tested.

Unlike some other methods described in the art, the results of present methods are not intended to be detected by eye. The principal reasons for this are so as to minimise human error and/or allow detection at levels generally less than discernable (or features smaller than discernable) by the human eye. Thus, any fluorescence is detected by appropriate photo-detectors known in the art.

Typically a spectrophotometer, commercially available microarray scanners or the like may be used to irradiate the areas of the array to which the antibodies are bound, at a first wavelength and any fluorescence detected, as a result of cells being bound to said antibodies, at a second longer wavelength.

Moreover, using appropriate electronics and software, any device can be programmed to know the identity and location of specific antibodies on the surface of the substrate and to correlate this with fluorescent signals generated, so that a particular blood grouping can be determined and identified to the tester. Additionally, statistical software may be included so as to combine and formulate the results from the various repetitions and/or dilutions of the antibodies provided on the substrate. In this manner, the fluorescent signals obtained from a multiplicity of specific antibody spots may be factored together and a statistically significant result displayed to the tester.

In a further aspect there is provided a method of determining whether or not a particular cell surface antigen is present in a sample of cells, comprising the steps of:

a) providing a sample comprising cells to be tested;

b) contacting said cells with a substrate comprising one or more antibodies bound thereto, wherein said antibodies are capable of specifically binding to specific cell antigens such as cell surface antigens which may be present on the cells;

c) allowing any cell antigens present in the sample to specifically react with said bound antibodies;

d) substantially removing any unbound cells and/or other material from at least an area of the substrate to which said antibodies are bound; and e) directly detecting any cells bound to said antibodies, in order to determine whether or not said cell surface antigen is present on the cells.

Suitable cells can include monocyte/macrophages, B cells, T cells, dendritic cells, NK cells, stem cells and microbes such as bacteria, fingi and parasites. Antigens to be detected may include proteins which may be expressed on cells displaying abnormal proliferation and/or aggregation, as may be observed, for example, in cancer, inflammation or abherant immunopathologies. Thus, the methods of the present invention may be of use in diagnosing cancer, inflammatory conditions or immunopathologies and/or to monitor such disease progression or treatment.

The present invention will now be described further, by way of example and with reference to the figures which show:

DETAILED DESCRIPTION

Example 1

Preparation of Arrays

Figure 1A:
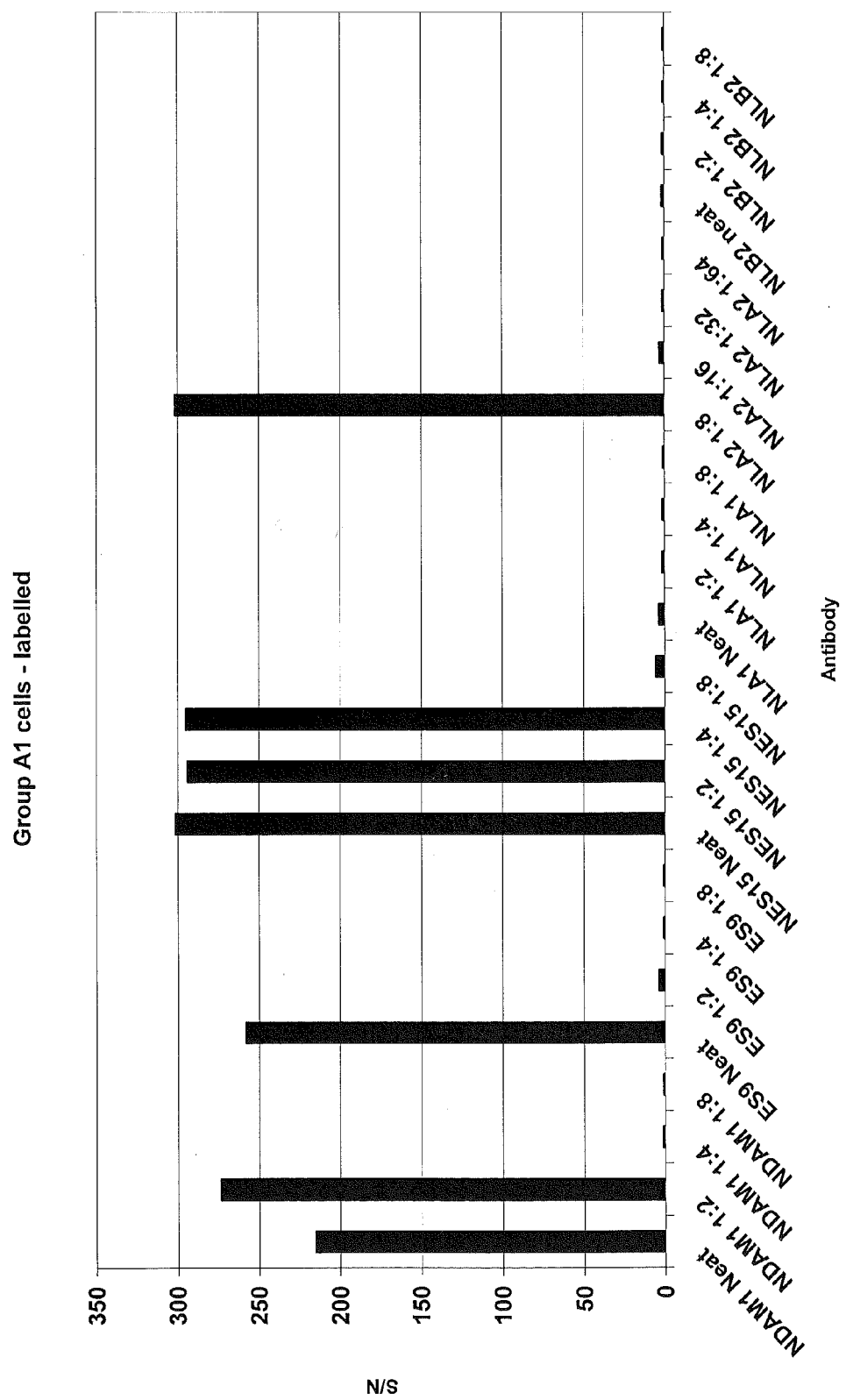
FIG. 1 shows reactivity profiles of fluorescently labelled erythrocytes with a microarray of antibodies a) group A cells; b) group B cells; c) group O cells.

Epoxy silane coated slides were prepared using standard glass microscope slides from Erie Scientific. The slides were cleaned in a caustic ethanol solution comprising:

Sodium Hydroxide 105 g
Water 420 mls
Ethanol 630 mls
for 2 hours with agitation. The slides were then rinsed twice in deionised water and centrifuged to dryness in an Eppendorf 5810R centrifuge at 1000 rpm for one minute. The slides were then placed in a solution of glycidoxypropyltriethoxy silane (1% v/v in 95:5 ethanol/water) for one hour with constant agitation. After rinsing twice in ethanol the slides were heated in an oven at 383 K for 15 minutes. After cooling, the slides were kept in a desiccated environment. Where used, other slide types were obtained from commercial sources. Gold slides from Erie Scientific or Ssens BV, Hydrogel slides from Schott or Full Moon.

Antibodies were deposited on these slides using solid pins of either 700 or 200 µm on a Microgrid II spotter from Biorobotics. The temperature for printing was 291±1 K and ≥30% humidity. Each antibody was present as four replicates.

After printing, the arrays were stored in a slide box and sealed under nitrogen. While not in use, arrays were stored at 278 K.

All the antibodies are derived from monoclonal hybridoma cell lines. Cell lines were prepared in-house according to standard protocols. Established cell lines were stored in aliquots frozen in liquid nitrogen. When required, the aliquots are aseptically thawed into DMEM/F12 media containing Foetal Calf Serum. The cells double approximately every 24 hours and the culture is expanded using the media until the desired volume is reached. During this time the conditions are maintained at those optimal for each cell line ($O_2$, $CO_2$, pH, temperature). Once the desired volume is reached the cells are maintained at the optimal conditions until cell viability falls below 30%. The antibody is then harvested by tangential flow filtration to rid the culture of cell debris. The harvested material is routinely concentrated to $\frac{1}{5}$ the volume by tangential flow filtration. From thawing to harvest of material (approx. 100 L grown in fermenter) the timescale is on average 4 weeks. Antibodies were purified by either gel filtration or by an affinity capture method. To assay both specificity and potency of the antibody, standard serological haemagglutination techniques are used. This involves adding a suspension of erythrocytes to the antibody and observing for visible clumping (haemagglutination). The presence or absence of haemagglutination is used to determine specificity. To perform potency the same principles are used but in this case the antibody undergoes doubling dilutions and is then tested with erythrocytes. Potency end points are used to describe potency.

Antibodies were chosen on the basis of established specificity as shown in the table below. The antibodies were purified by chromatography and their solution phase agglutination properties and microarray reactivities correlated (Table 1). Antibodies were typically printed at four different dilutions per chip.

TABLE 1

Antibodies used for printing microarrays.

| Antibody Reference | Specificity | SDS PAGE | Post column potency | Microarray S/N |
|---|---|---|---|---|
| LA1 | Anti-A | Distinct heavy and light bands (very little impurities) | Good, $\frac{1}{256}$ | 3.5 Neat |
| LA2, | Anti-A | Distinct heavy and light bands | Very Good, $\frac{1}{4}$K | 301 at 1:8 dil |
| ES9, | Anti-A | Heavy and light bands not obvious | Ok, $\frac{1}{32}$ | 258 neat |
| DAM1, | Anti-A | Heavy and light bands not obvious | Good, $\frac{1}{512}$ | 215 neat |
| LB2, | Anti-B | Distinct heavy and light bands | Very Good, $\frac{1}{4}$K | 96 neat |
| ES15, | Anti-A(B) | Distinct heavy and light bands | Very Good, $\frac{1}{4}$K | 301 Neat |
| LB3 | Anti-B | Heavy and light bands not obvious | Poor | 1.5 |

Example 2

Microarray Experiments

Prior to use, the arrays were blocked in Bovine Serum Albumin (BSA); this is generally considered to reduce non-specific binding to the array surface.

To block, the slides were rinsed briefly in Phosphate Buffered Saline (PBS) pH 7.0 containing 1% Bovine Serum (BSA) and 0.1% Tween 20 by vigorously submerging 10 times. They were then placed into a fresh container of PBS pH 7.0 containing 1% BSA for one hour at room temperature, with constant mixing.

The slides were rinsed briefly in PBS pH 7.0 (submerged 10 times) and centrifuged to dryness in an Eppendorf 5810R centrifuge at 1000 rpm for one minute.

Blood samples Were incubated on the array using hybridisation chambers from Schleicher and Schuell (approximate capacity: 450 µl). Blood samples were incubated on arrays for 1 hour at room temperature with constant shaking. After incubation, the hybridisation chambers were removed and the slides washed in a mixture of PBS and Tween 20 (1%) by vigorously submerging them ten times. The slides were then rinsed twice in deionised water and centrifuged to dryness in an Eppendorf 5810R centrifuge at 1000 rpm for one minute.

Scanning was carried out using a Scanarray 5000 confocal microarray scanner from Packard Biochip Technologies. For each array, five scans were taken using consistent pmt setting and incrementally increasing laser power settings. Arrays were analysed using Quantarray software. From the five scans of each slide, the optimal scan in terms of linear range was selected on the basis of comparative scatter plot analysis.

A signal to noise ratio (S/N) was calculated for each antibody spot. The noise level was determined for each slide by taking the average fluorescent intensity plus two standard deviations of the PBS spots (negative controls since no cells should be specifically bound). The signal to noise ratio was then calculated by dividing the fluorescence intensity for each spot by the noise. For each group of replicate spots, a median value was obtained.

Results

Figure 1B:
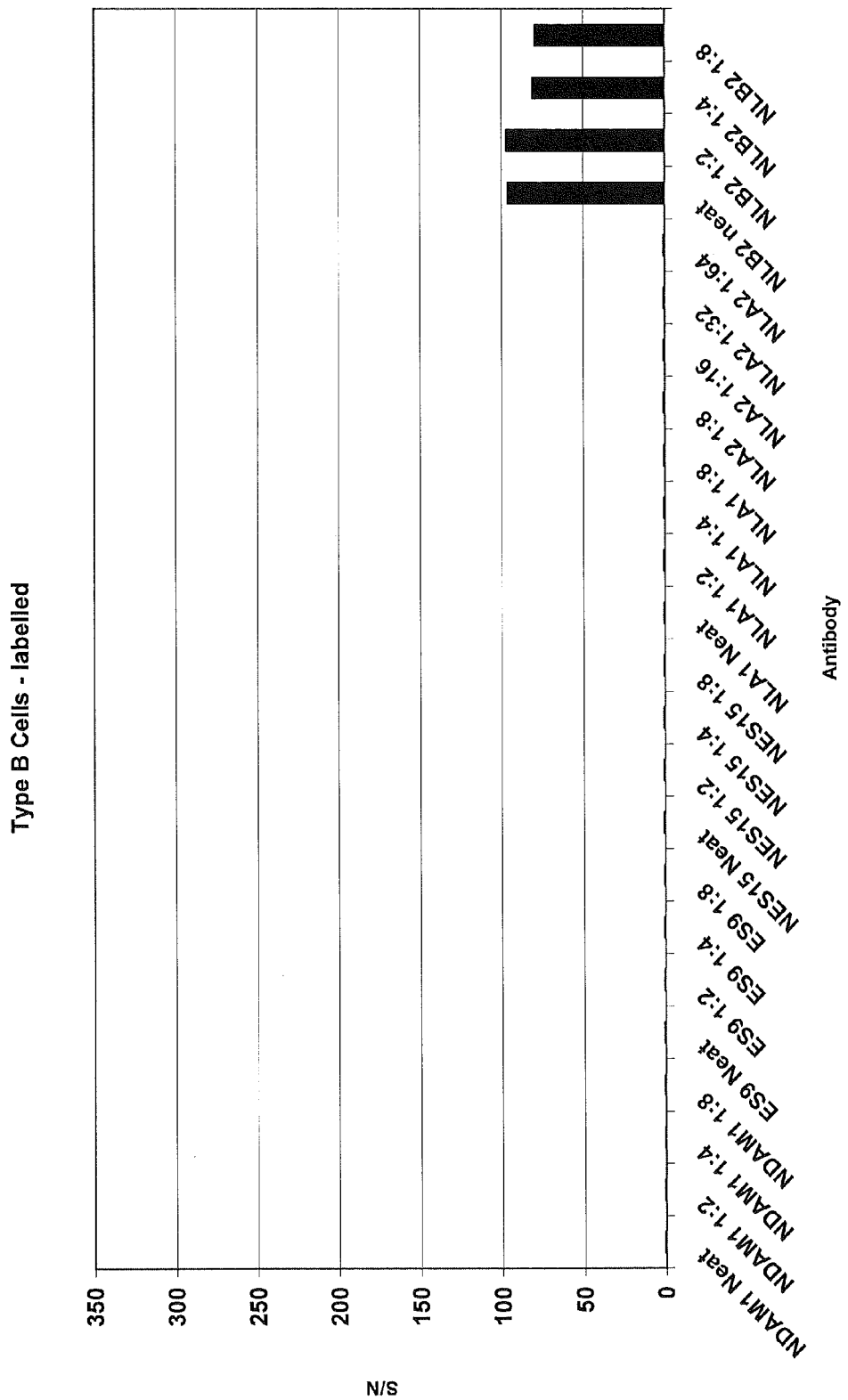
Figure 1C:
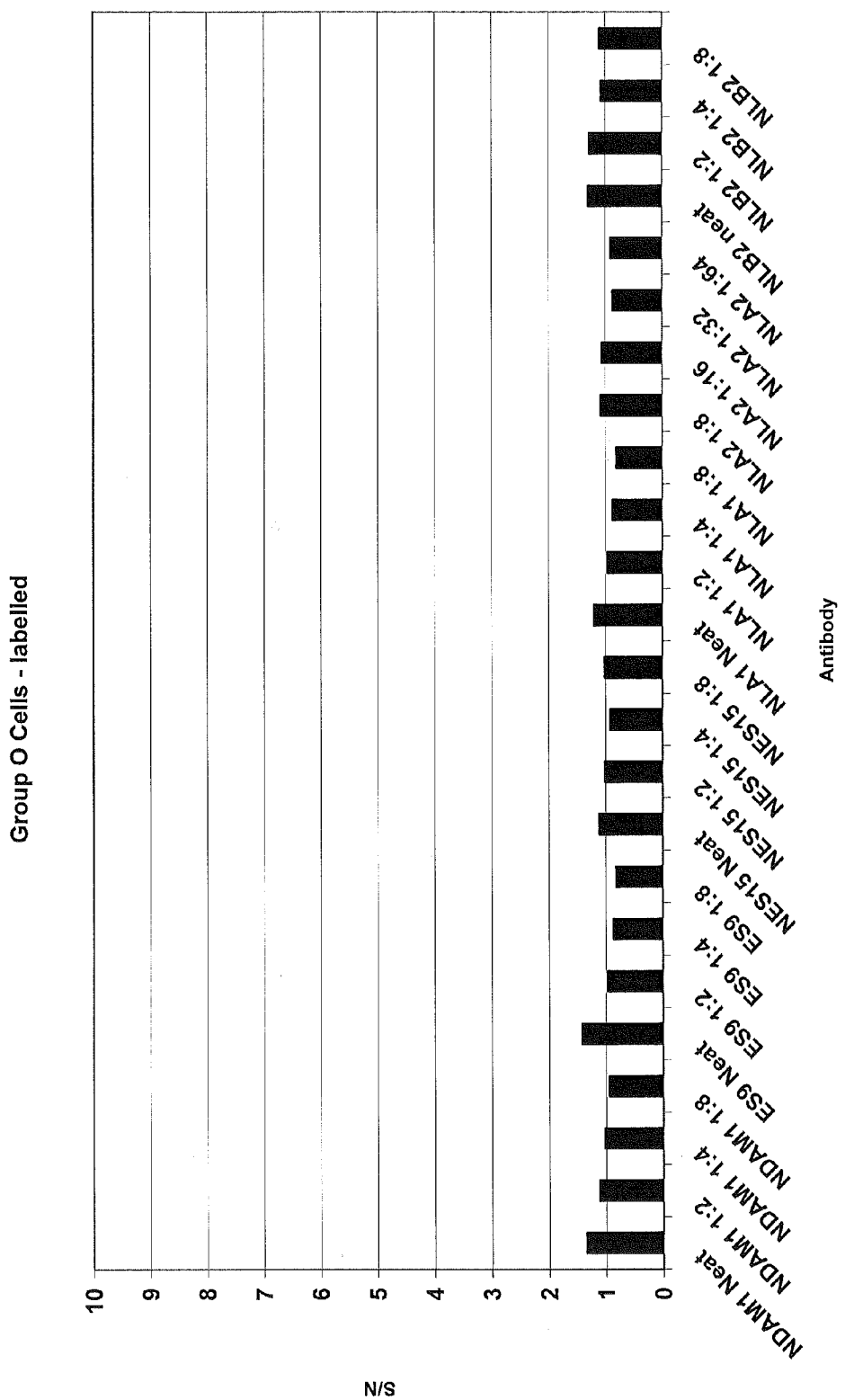

Microarray experiments using an array of antibodies attached to an epoxysilane surface have shown that multiplexed blood typing can differentiate between common A, B and O blood groups. FIG. 1(*a-c*) shows how the antibody reactivity pattern expressed as a signal to noise ratio differs for each of these blood groups when using purified, labelled red blood cells (note the difference in scale).

Using purified and labelled cells to type blood on a microarray requires several sample preparation and derivatisation steps. In order to simplify this procedure, the present inventors attempted to type whole blood and thus dispose of some blood pre-treatment steps. The present inventors attempted to label whole blood using fluorescein isothiocyanate (FITC) and then incubate this on an array in the expectation that the fluorescently labelled red cells would be quantifiable where they had bound to antibody spots. Although red cells were clearly bound to the spots and were visible by eye, when scanned using FITC settings the fluorescence from the background between the spots was so strong that it overpowered the specific signal from the spots.

This can probably be explained by considering the make up of the blood proteome. About 40% of the human serum proteome is Human Serum Albumin and this will be fluorescently labelled at the same time as the red cells since FITC non specifically labels all proteins. HSA is known to bind non-specifically to a lot of proteins and in such high concentrations a relatively weak interaction can be responsible for the high background between the antibody spots. In order to get around this problem in whole blood typing, the present inventors looked at whether the fluorescent signal caused by the intrinsic fluorescence of the red blood cells is enough to quantify the binding reaction.

Figure 2A:
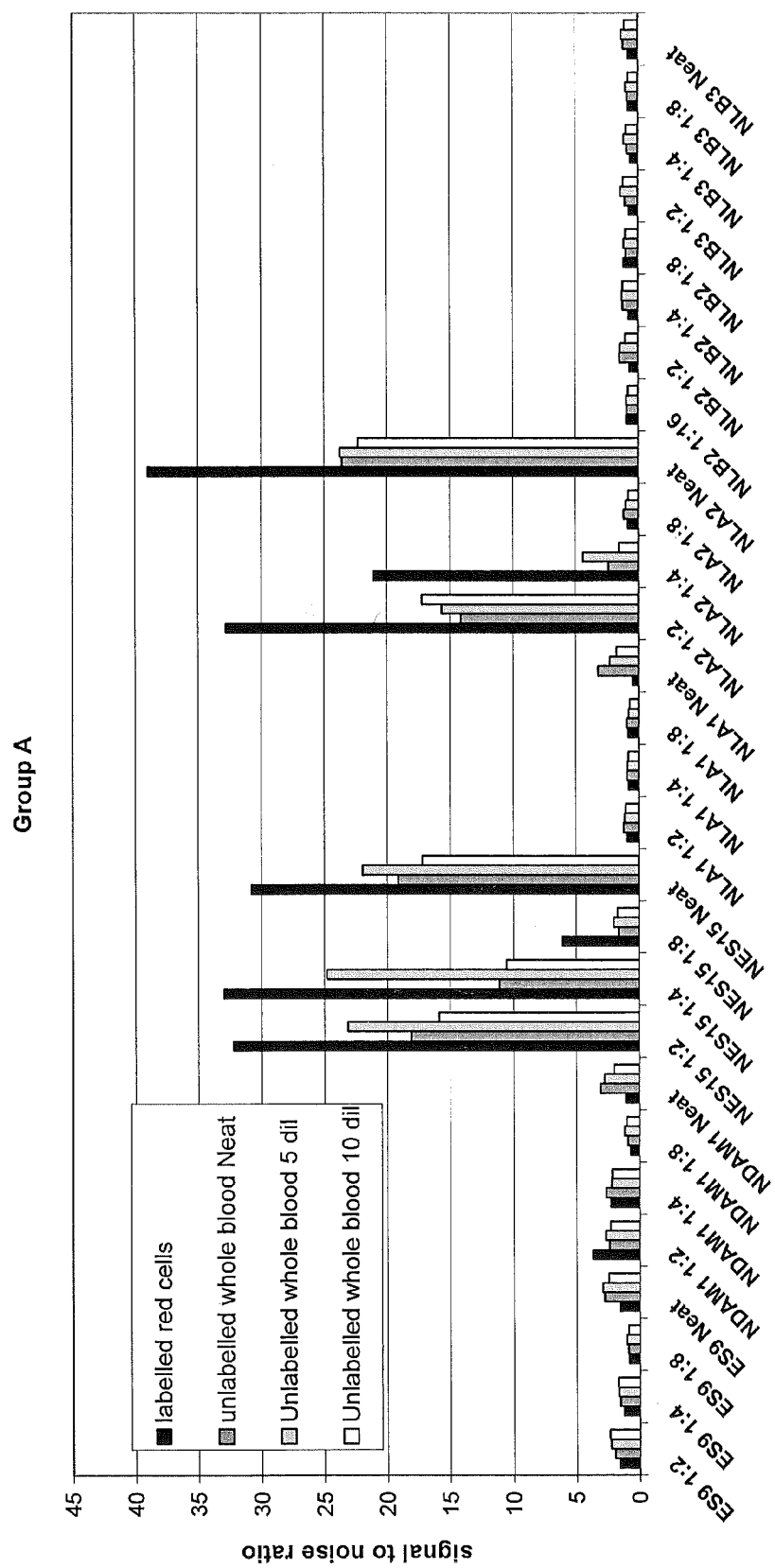
FIG. 2 shows a comparison of blood samples for use in an array based typing experiment: a) Type A, b) Type B, c) Type O.
Figure 2B:
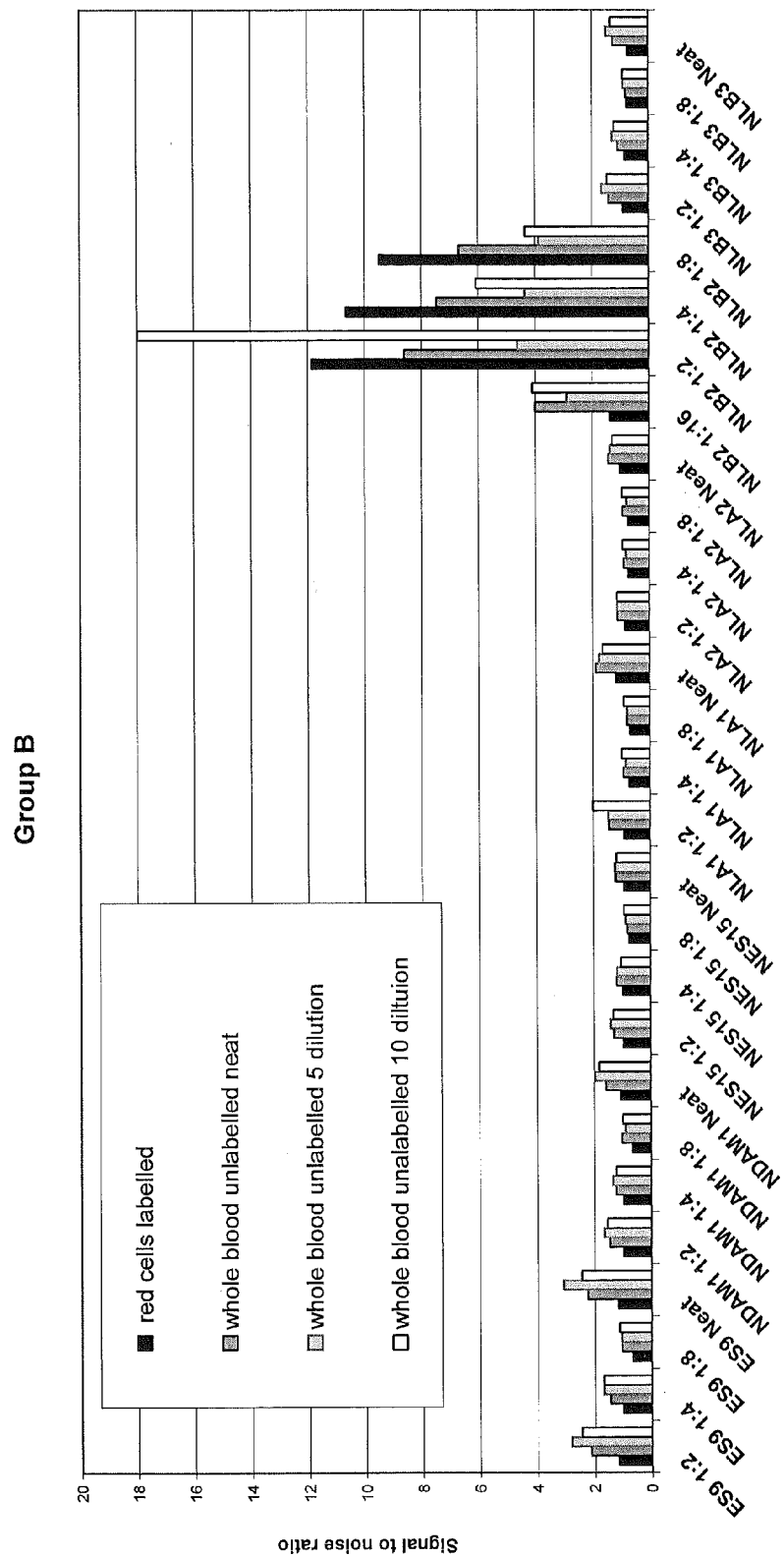
Figure 2C:
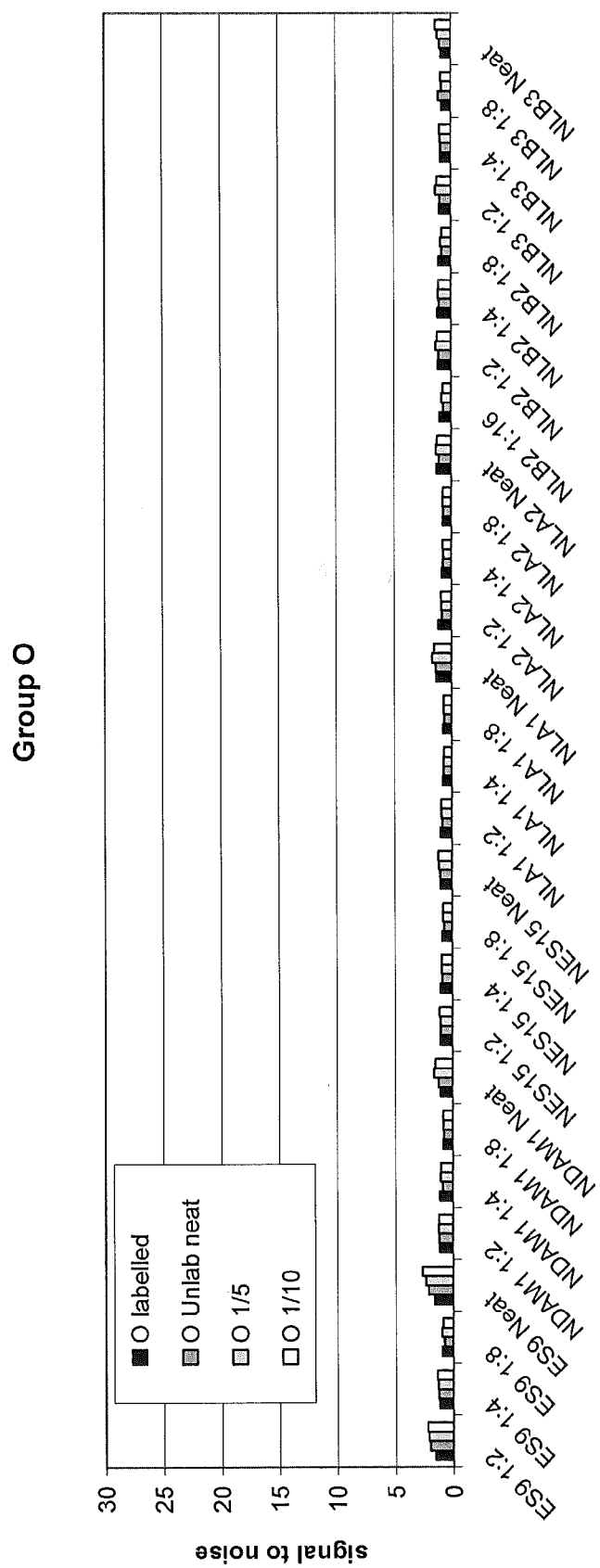

FIG. 2 is a graph showing the reactivity of an array of antibodies with labelled red cells, whole blood, whole blood diluted 1:5 with PBS and whole blood diluted 1:10 with PBS. It can be seen from this graph that the pattern of reactivity is the same for the labelled cells as for the whole blood but that the signal intensity varies with treatment. If can also be seen that in all cases, the signal to noise rations are high enough to allow discrimination between type A, B an O blood. For type A cells, 1:5 diluted blood appears to have the highest S/N ratio but for B the neat whole blood has the highest S/N.

Example 3

Optimisation of Scanning Conditions

Figure 3:
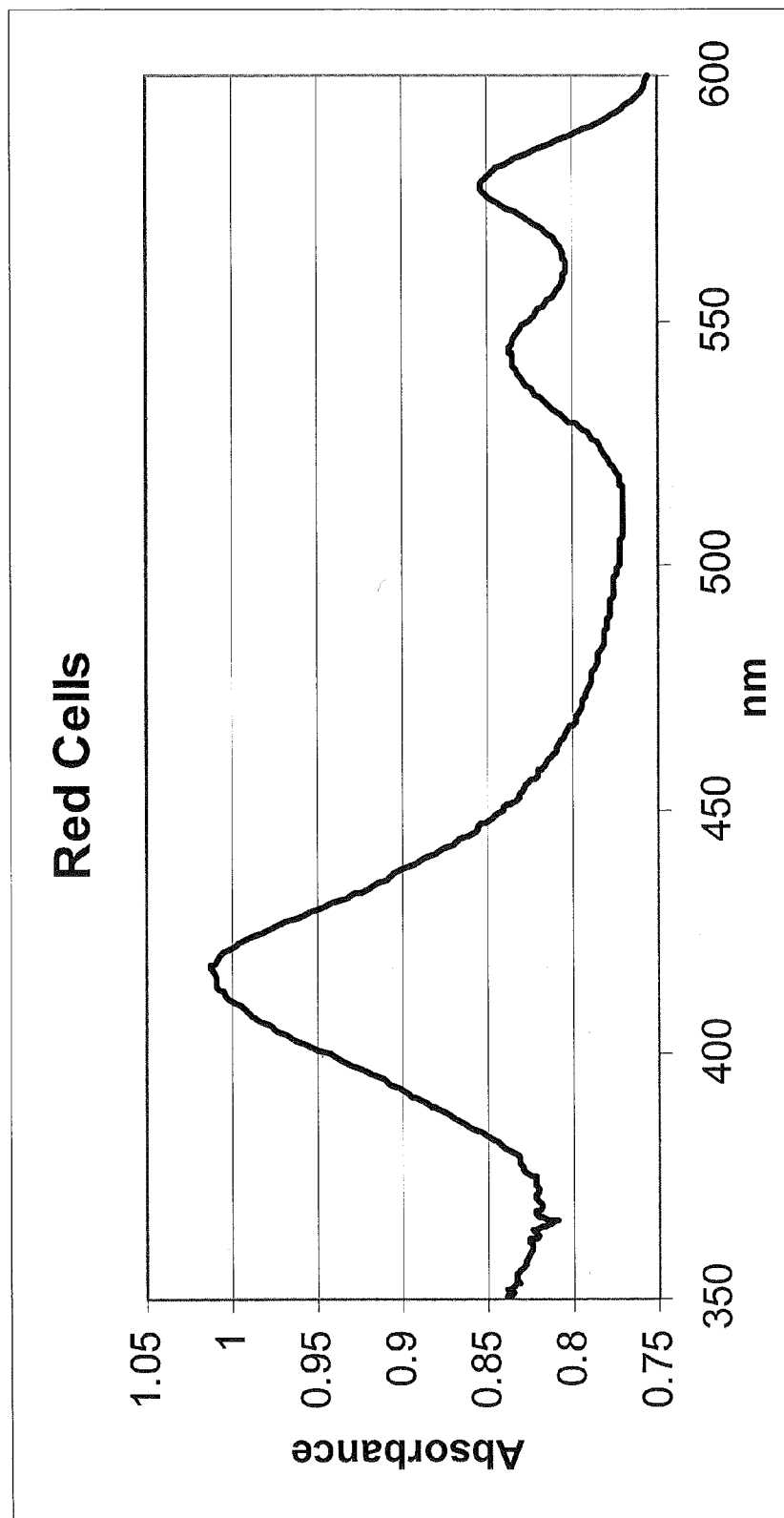
FIG. 3 shows the absorbance spectrum of red blood cells.
Figure 4A:
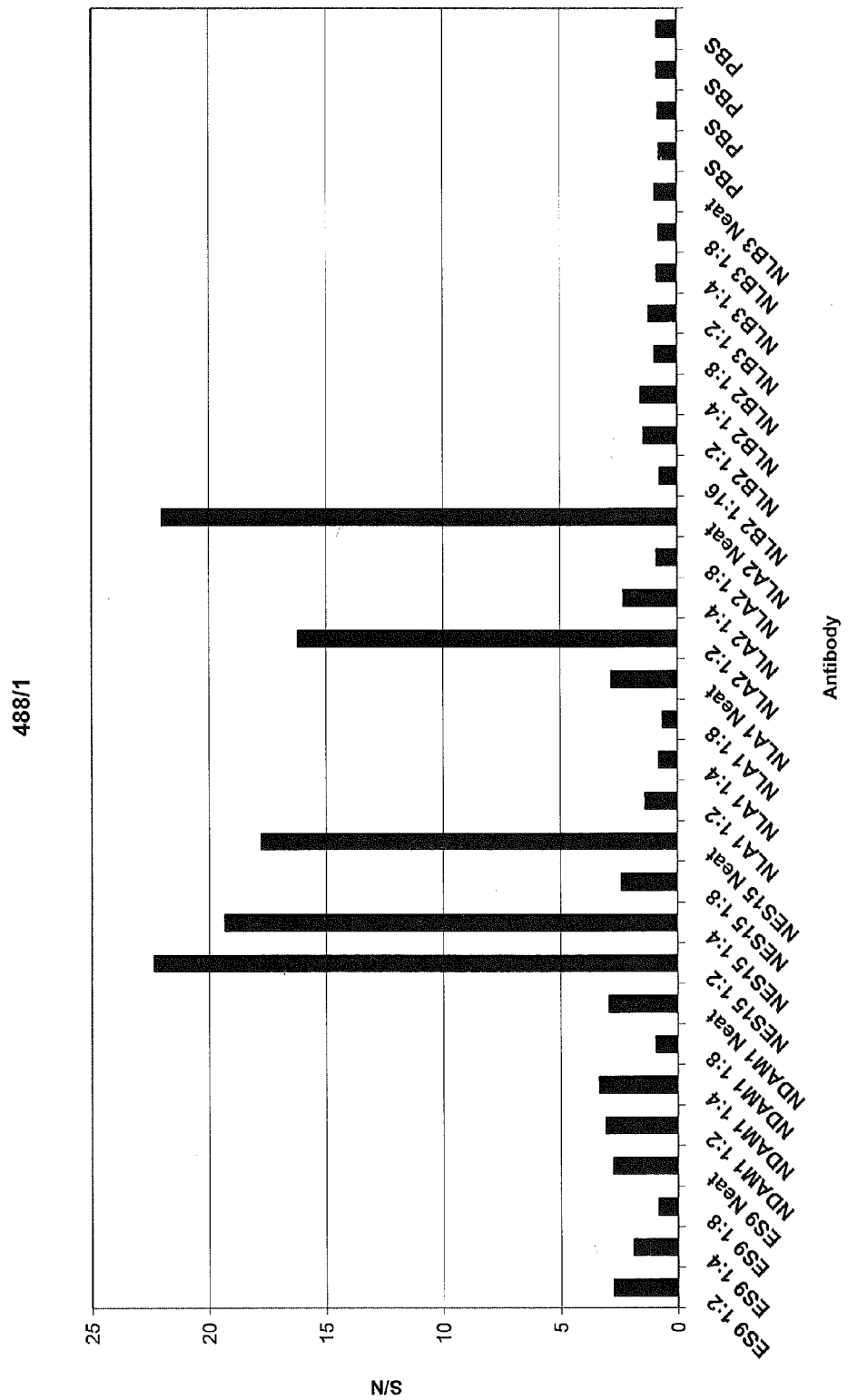
FIG. 4 shows a comparison of scanning protocols of label-free blood typing microarrays (see table 2), a) 488/1, b) 543/1, c) 543/2, d) 543/3, e) 488/1.
Figure 4B:
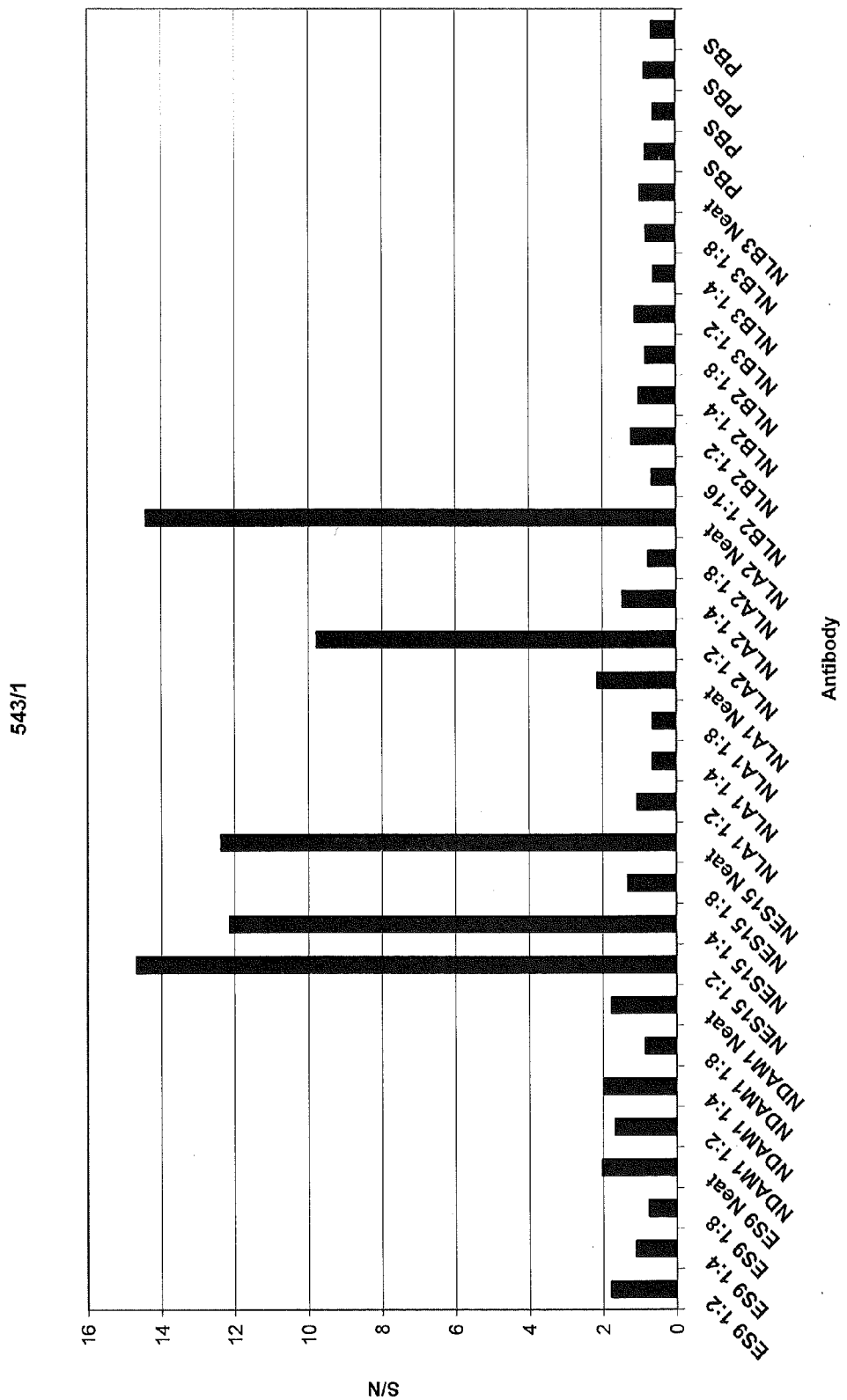
Figure 4C:
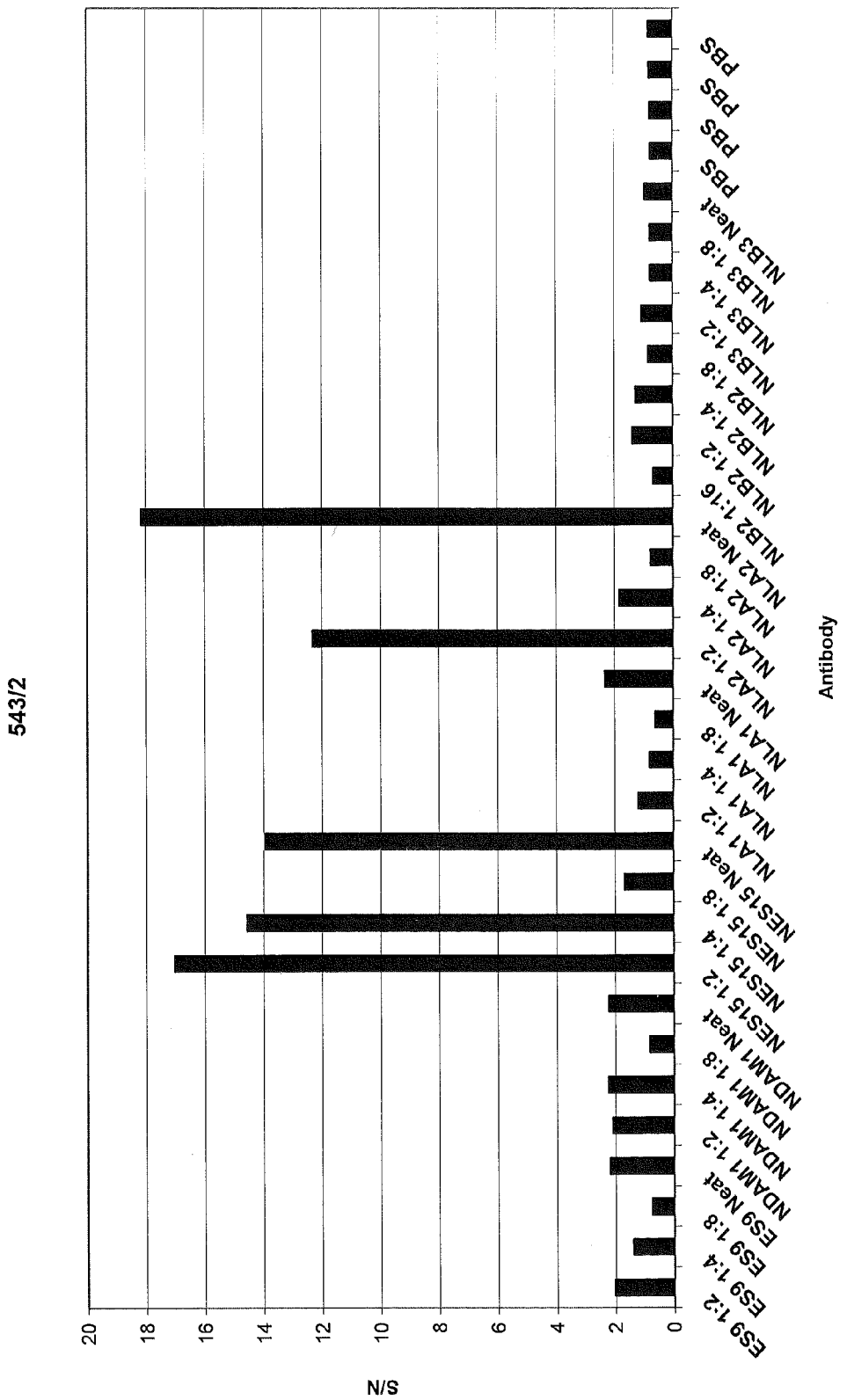
Figure 4D:
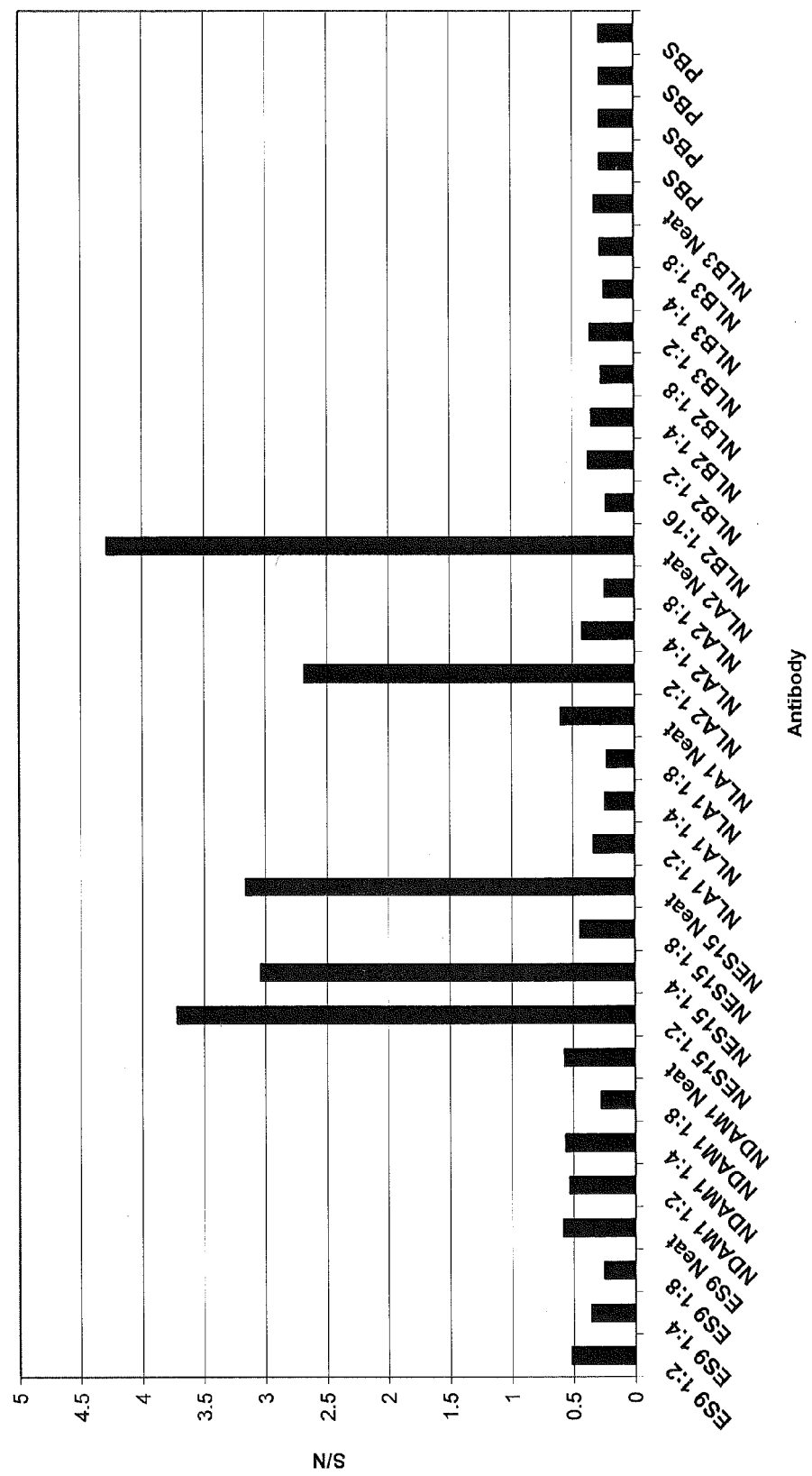
Figure 4E:
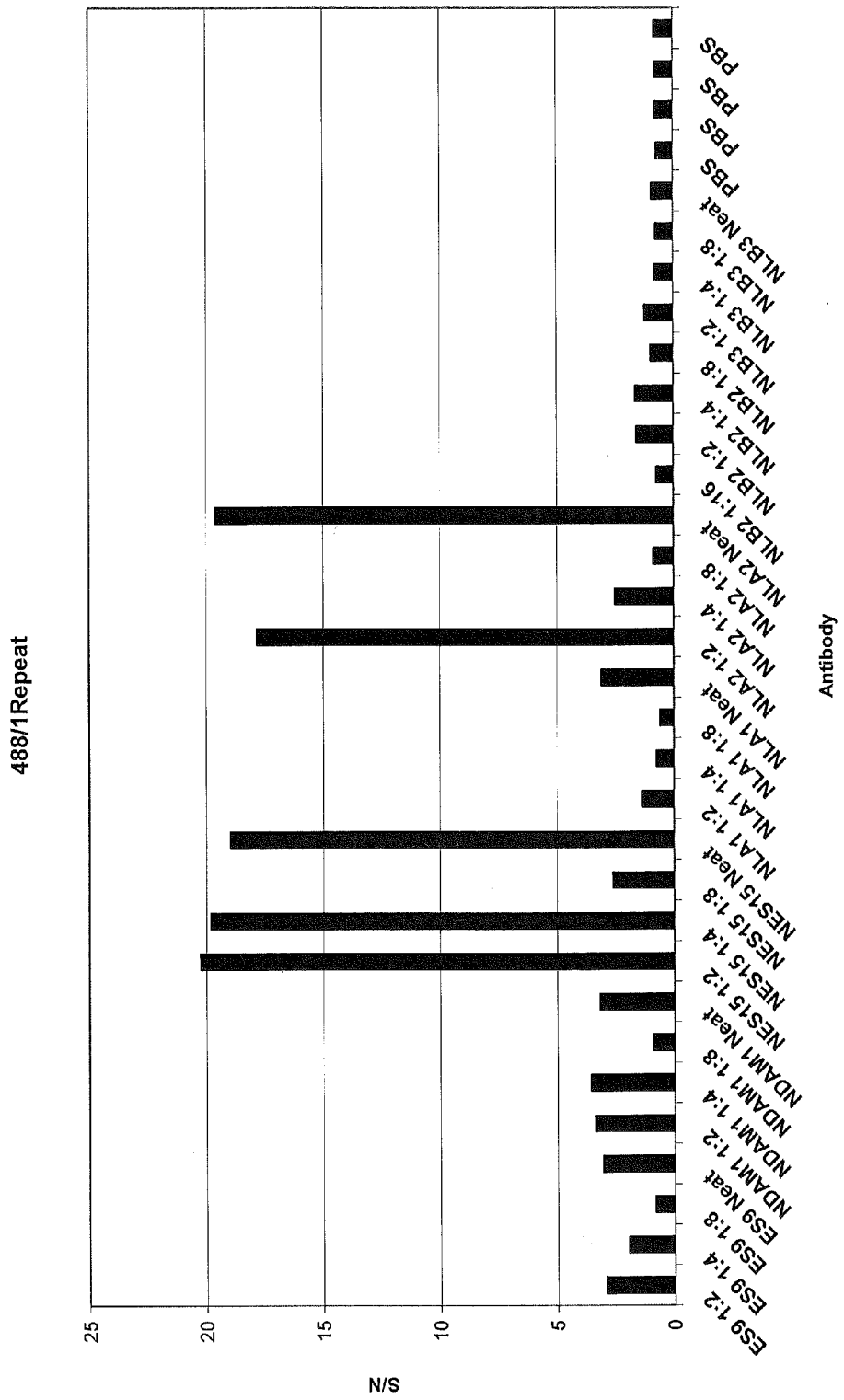

Red Blood Cells have an Absorbance Spectrum as Shown in FIG. 3.

This absorbance spectrum is typically of oxy-haemoglobin, as would be expected with native red blood cells. Since the present inventors originally thought that haemoglobin species would be responsible for the fluorescence of erythrocytes, they tried to maximise the fluorescent signal by tuning the excitation wavelength to the absorbance spectrum shown in FIG. 3. In their initial experiments, using fluorescein labelled cells, they used scanner settings for fluorescein (excitation 488 nm, emission 530 nm). Since unlabelled red blood cells absorb strongly at 420, 540 and 580 nm, they would expect one of these wavelengths to give the strongest fluorescence when excited. The peak at 420 nm has the strongest absorbance but since commercial microarray scanners do not have lasers which can excite at this wavelength, the lowest excitation available was 488 nm. The present inventors compared the signal to noise ratio for this setting with three other settings which excite at the 543 nm (close to the absorbance peak) as detailed in Table 2.

TABLE 2

Wavelengths used for comparison of scanner settings

|  | Excitation wavelength (nm) | Detection wavelength (nm) |
|---|---|---|
| Case 488/1 | 488 | 530 |
| Case 543/1 | 543 | 570 |

TABLE 2-continued

Wavelengths used for comparison of scanner settings

|  | Excitation wavelength (nm) | Detection wavelength (nm) |
|---|---|---|
| Case 543/2 | 543 | 578 |
| Case 543/3 | 543 | 585 |

The signal to noise ratios obtained using these settings are shown in FIG. 4. After scanning, the 488/1 scan was repeated to ensure that deleterious bleaching of fluorescence could be controlled for.

It can be seen that although there is a little variability between the S/N from the two 488 nm scans, both are higher than the settings using excitation at 543 nm. The reason for this may be that the higher energy (low wavelength) light excites more autofluorescence from the cell wall and other components as well as the haemoglobin and thus gives a higher overall signal. However, since these cellular components are specific to the cells and not the background area between the spots, the best signal to noise is seen using 488 nm excitation scanner settings.

Example 4

Further Evaluation of a Protein Microchip Method for Typing Whole Blood

Experiment Summary: A total of 67 Gold microarray slides (Ssens BV) were printed with antibodies specific for A (LA2-SF, 159 separate spots per array) and B (LB2, 224 separate spots per array) blood type antigens. A total of 67 whole blood samples (A=26, B=8, O=33) were obtained from donors and used with the donors' prior consent and ethical clearance was obtained. Individual blood samples were diluted 1/40 in phosphate buffered saline and added to the arrays for a one hour incubation at room temperature with regular shaking at 5-min intervals.

Slides were scanned with a ScanArray 5000 confocal microarray scanner from Packard Biochip Technologies. For each array five scans were taken using a consistent PMT setting and incrementally increasing laser power settings. Microarray images were analysed with Quantarray software using the fixed circle method and subtracting the background fluorescence from the spot value (Signal-Background). From the five scans of each slide, the optimal scan in terms of linear range was selected on the basis of comparative scatterplot analysis (Forster, Roy & Ghazal, 2003 Journal of Endocrimology. 178: 195-204).

Figure 5:
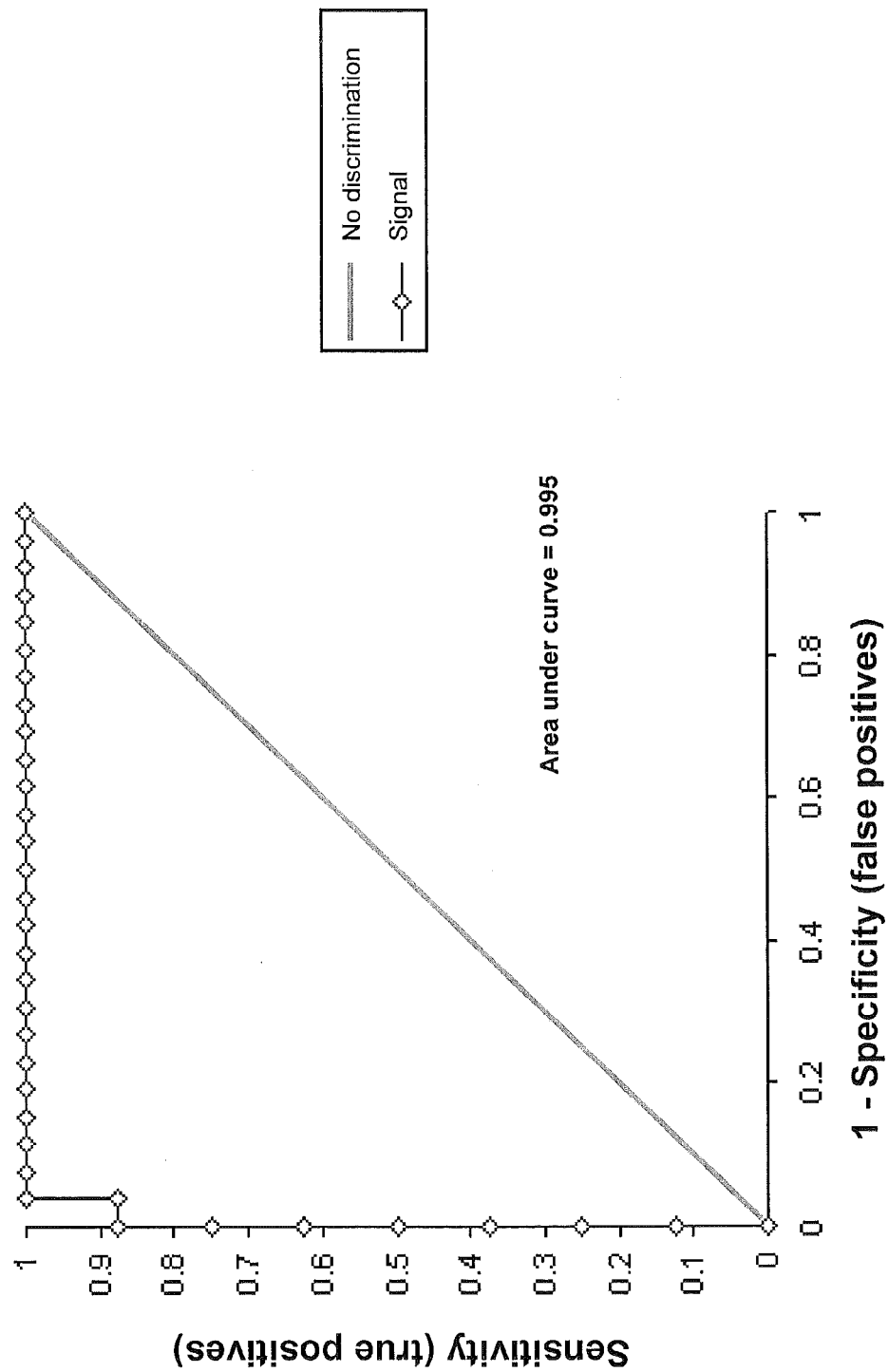
FIG. 5 shows a Receiver Operator Characteristic (ROC) Curve of Sensitivity vs. (1-Specificity), example shown is of the Index Scores of the A blood type samples (True Positives) against the B blood type samples (False Positives)

The Signal-Background value for each replicate spot was obtained and the median of these values for each probe was used for the comparative analysis. An Index Score was obtained for each array where the median Signal-Background value for the LA2-SF probe was divided by the median for the LB2 probe, giving a ratio value for the two responses. Receiver Operator Characteristic (ROC) Curves (sensitivity vs. (1-specificity)) were used to obtain threshold values (See FIG. 5).

The ROC curves showed that the derived LB2/LA2-SF ratio has a good ability to discriminate between A and B blood types. Further ROC curves were prepared to obtain thresholds for the B blood type and for the O versus the A and the O versus the B blood types and the area under each of these ROC curves is displayed in Table 3.

TABLE 3

Area under the ROC curves for each
of the blood type comparisons

| Blood Type | Area under ROC curve |
|---|---|
| A | 0.995 |
| B | 0.995 |
| O versus A | 0.986 |
| O versus B | 0.890 |

These threshold values were then used to assign blood type based on the Index Score value for each array (See Table 4).

TABLE 4

Threshold values of Index Scores for each blood
type were obtained following ROC curve analysis

| Blood Type | Threshold Value Selected of Index Score from ROC Curve | Percentage Sensitivity at Threshold | Percentage Specificity at Threshold |
|---|---|---|---|
| A | ≥2.71 | 100 | 96.2 |
| B | ≤0.64 | 100 | 87.5 |
| O | 0.929-2.7 | 87.5 (at 0.929) 92.3 (at 2.7) | 100 (at 0.929) 97 (at 2.7) |

Figure 6:
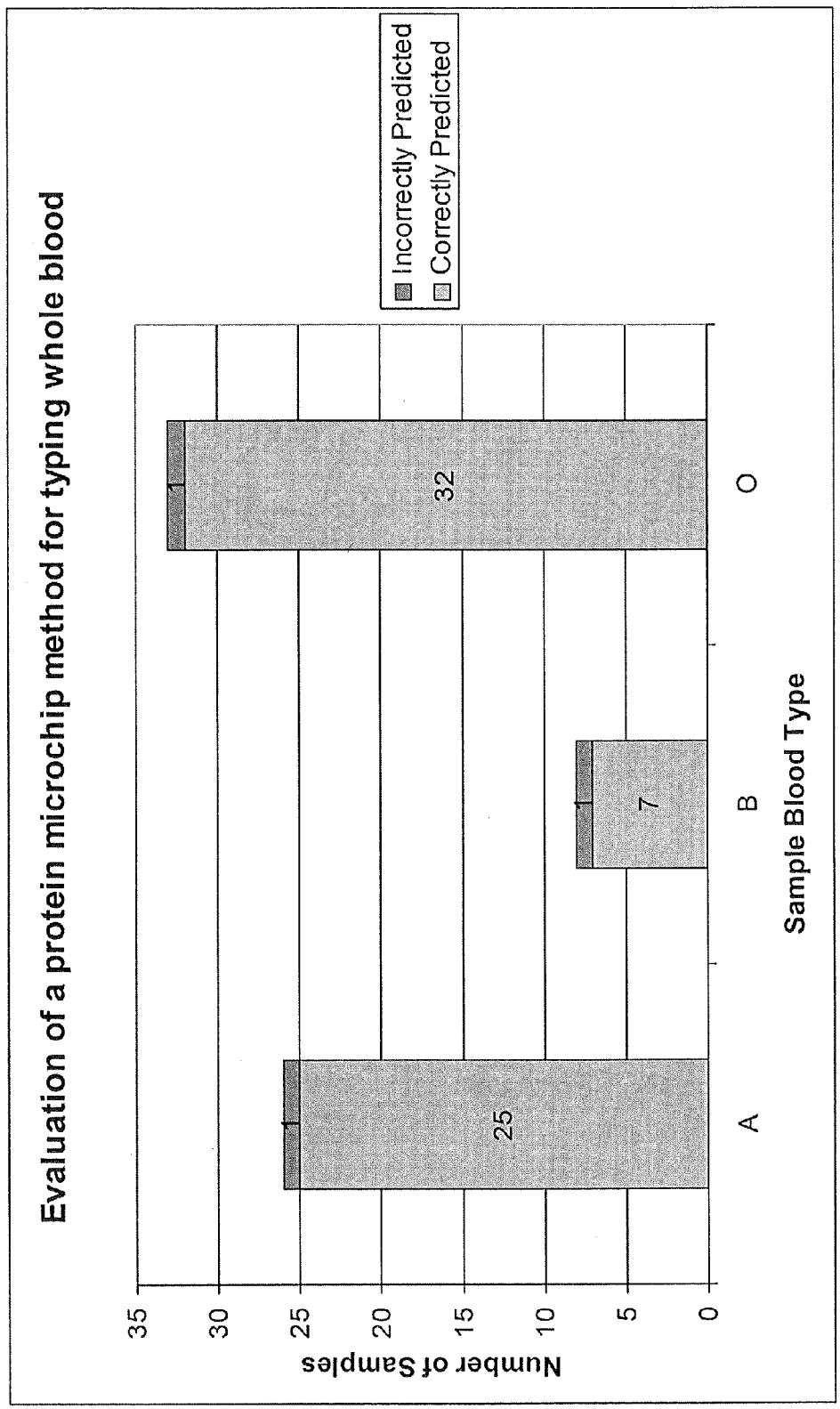
FIG. 6 shows an Evaluation of a protein microchip method for typing whole blood.

Based on these threshold values each of the 67 arrays was assigned a blood type without prior knowledge of the individual blood sample origins. A response of either 'Call' or 'No Call' was assigned to each array for each of the possible blood types based on the threshold values above. A correctly predicted sample was one that received a correct 'Call' for only the correct blood type, whilst an incorrectly predicted sample was one that received a 'No Call' for the correct blood type and a 'Call' for the incorrect blood type (See Table 5). This data is presented graphically below as a representation of the number of individual blood samples correctly and incorrectly predicted for each blood type (See FIG. 6).

TABLE 5

Number of blood samples correctly or incorrectly predicted using
the threshold values of index scores for each blood type. NB - All
samples received a 'Call' for a particular blood type.

| Classification | A | B | O | Total Samples |
|---|---|---|---|---|
| Total Samples | 26 | 8 | 33 | 67 |
| Correctly Predicted | 25 | 7 | 32 | 64 |
| Incorrectly Predicted | 1 | 1 | 1 | 3 |
| Percentage of Samples Correctly Predicted | 96.2 | 87.5 | 96.9 | 95.5 |

The invention claimed is:

1. A method for determining a blood group of a sample of blood, comprising the steps of:
a) providing a sample of blood comprising red blood cells to a device which comprises a substrate comprising one or more binding agents bound thereto, wherein: said binding agents are capable of specifically binding to specific red blood cell group antigens which may be present on said red blood cells; the binding agent is antibody or antibody fragment specific for said antigen(s) to be detected; said binding agents are bound to the substrate in the form of an array; and each specific binding agent is provided in a number of dilutions and/or repeated a number of times in order to minimise any false positive or negative reactions which may occur when carrying out the method of detection;
b) allowing any red blood cell antigens present on said red blood cells to specifically react with said bound binding agents;
c) substantially removing or reducing any unbound red blood cells from at least an area of the substrate to which said binding agents are bound; and
d) directly detecting any red blood cells bound to said binding agents in order to determine a subjects blood group,
wherein detection of any red blood cells bound to said binding agents is carried out by exposing the bound red blood cells to light at a first wavelength and detecting the intrinsic fluorescence of the red blood cells at a second longer wavelength,
and wherein the red blood cells are irradiated or excited at 543 nm and detection is carried out at 570-585 nm.

2. The method according to claim 1, wherein the blood group antigen to be determined is from the ABO and/or D (Rhesus) systems.

3. The method according to claim 1, wherein the blood group antigen to be determined is from the blood group antigen detectable using appropriate specific reagents systems selected from the group consisting of Kell, Duffy, Lewis, Kidd and Fisher blood group systems.

4. The method according to claim 1, further comprising the use of a positive control to ensure that red blood cell antigens are able to bind to said binding agent.

5. The method according to claim 1, wherein the substrate is made of glass, silicon, silicon oxide, metals and metal oxides either bare or functionalised with functional polymers.

6. The method according to claim 1, wherein the substrate is a gold coated substrate.

7. The method according to claim 6, wherein the gold is functionalised such that the binding agents are capable of being bound thereto.

8. The method according to claim 7, wherein the functionalisation is such that a distance between the gold surface and any bound red blood cell can be controlled.

9. The method according to claim 1, wherein the array is formed on a planar or spheroid substrate.

10. The method according to claim 1, wherein the substrate is a rigid or semi-rigid support selected from the group consisting of membranes, filters, chips, slides, wafers, fibers, magnetic beads, nonmagnetic beads, gels, tubing, plates, polymers, microparticles and capillaries.

11. The method according to claim 10, wherein the substrate includes a modified surface architecture.

12. The method according to claim 1, wherein said binding agents are spotted, printed or otherwise bound to the substrate.

13. The method according to claim 1, wherein the substrate comprises a plurality of separate arrays on the surface of the substrate, arranged in a manner to allow separate samples to be contacted with each array in such a way such that the samples do not mix and in order that more than one sample may be tested.

14. The method according to claim 1, wherein unbound material is removed by washing the surface of the substrate with a solution such as water or saline, by blowing or sucking air across the surface of the substrate, or by using centrifugation, or shaking to dispel unbound material from the surface of the substrate.

15. The method according to claim 1, wherein any fluorescence is detected by a photo-detector.

16. The method according to claim 1, wherein statistical software is utilised so as to combine and formulate results from various repetitions and/or dilutions before displaying/providing a result to the tester.

17. The method according to claim 1, wherein detection is carried out at 570 nm.

18. The method according to claim 1, wherein detection is carried out at 578 nm.

* * * * *